United States Patent
Lipshitz et al.

[11] Patent Number: 5,354,335
[45] Date of Patent: Oct. 11, 1994

[54] INTRAOCULAR INSERT FOR IMPLANTATION IN THE HUMAN EYE

[76] Inventors: Isaac Lipshitz, 89A Hanassi Street, 46 399 Herzlia; Joseph Gross, 73 160 Moshav Mazor, both of Israel

[21] Appl. No.: 13,387

[22] Filed: Feb. 4, 1993

[51] Int. Cl.⁵ .............................................. A61F 2/16
[52] U.S. Cl. ........................................ 623/6; 351/158; 351/160 R
[58] Field of Search ............... 623/6; 351/158, 160 R

[56] References Cited

U.S. PATENT DOCUMENTS

| | | | |
|---|---|---|---|
| 4,666,446 | 5/1987 | Koziol et al. | 623/6 |
| 4,955,902 | 9/1990 | Kelman | 623/6 |
| 5,030,231 | 7/1991 | Portney | 623/6 |
| 5,044,743 | 9/1991 | Ting | 623/6 X |
| 5,074,875 | 12/1991 | Donn et al. | 623/6 |
| 5,196,028 | 3/1993 | Portney et al. | 623/6 |
| 5,275,623 | 1/1994 | Sarfarazi | 623/6 |

*Primary Examiner*—Randall L. Green
*Assistant Examiner*—Mary Beth O. Jones
*Attorney, Agent, or Firm*—Benjamin J. Barish

[57] ABSTRACT

An intraocular insert for implantation in the interior of a human eye, characterized in that the insert includes a converging lens to face the anterior side of the eye, and a diverging lens in alignment with and spaced behind the converging lens to face the posterior side of the eye.

20 Claims, 1 Drawing Sheet

INTRAOCULAR INSERT FOR IMPLANTATION IN THE HUMAN EYE

FIELD AND BACKGROUND OF THE INVENTION

The present invention relates to an intraocular insert for implantation in the interior of the human eye to replace the human crystalline lens.

Macular degeneration is a disorder in which the central retinal area (the macula) degenerates, e.g., because of age (age-related macular degeneration, or AMD), diabetic retornopathy, ocular vascular accidents, retinal dystrophies as for example cone dystrophy, central nervous system (CNS) diseases, etc. These disorders in the macular area cause difficulty in vision such that the afflicted person is unable to read without special telescopic or microscopic eyeglasses that create a magnification of the object on the retina. However, when an outside telescope is used, the visual field is very narrowly restricted, and therefore the afflicted person has to move his or her head back and forth to follow the lines being read.

OBJECT AND SUMMARY OF THE INVENTION

An object of the present invention is to provide a novel intraocular insert for implantation in the interior of the human eye particularly for use by persons suffering from macular degeneration diseases.

According to the present invention, there is provided an intraocular insert for implantation in the interior of a human eye, characterized in that the insert includes a converging lens carried by the insert to face the anterior side of the eye; and a diverging lens carried by the insert in alignment with and spaced behind the converging lens to face the posterior side of the eye.

More particularly, and according to the preferred embodiments of the invention described below, the insert includes a converging lens to face the anterior side of the eye; and a diverging lens in alignment with and spaced behind the converging lens to face the posterior side of the eye.

An intraocular insert constructed in accordance with the foregoing feature increases the visual field that the patient enjoys. Moreover, it obviates the need of using an outside telescope, and therefore the need for the patient to move the head back and forth when scanning lines being read. A further advantage in implanting the above intraocular device, to replace the human crystalline lens, is that it enables the patient also to use outside magnification (e.g., spectacles or contact lenses) in combination with the intraocular insert to achieve higher magnification than possible by using just magnifying spectacles or contact lenses alone.

Further features and advantages of the invention will be apparent from the description below.

BRIEF DESCRIPTION OF THE DRAWINGS

The invention is herein described, by way of example only, with reference to the accompanying drawings.

DESCRIPTION OF PREFERRED EMBODIMENTS

Figure 1:
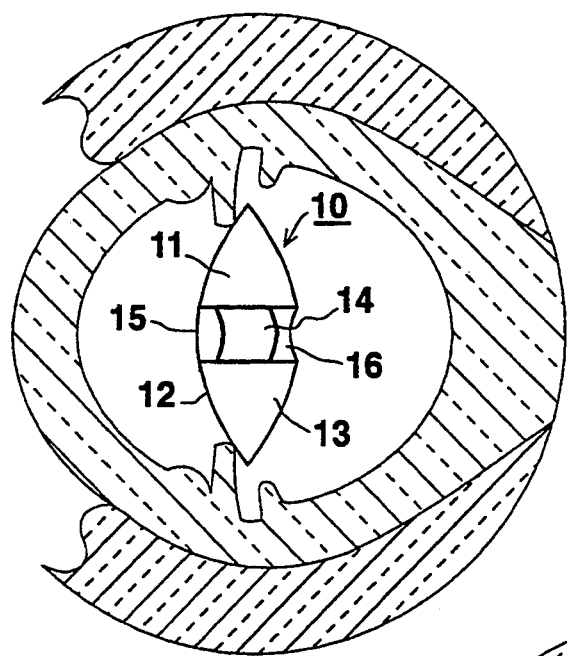
FIG. 1 is a horizontal section through the eye illustrating a first embodiment of intraocular insert constructed in accordance with the present invention.

With reference first to FIG. 1, there is illustrated a horizontal section of a human eye, including one form of intraocular insert, generally designated 10, constructed in accordance with the present invention. The means for fixing the insert 10 in the eye are not described herein, as many such means are known for mounting artificial intraocular lenses and can be used for fixing the intraocular insert 10.

The intraocular insert 10 includes a body member 11, of generally convexo-convex or convexo-plano configuration; that is, its front or anterior face 12 facing the anterior side of the human eye is of convex configuration, and similarly its rear or posterior face 13 facing the posterior side of the human eye is of convex (or planar) configuration.

The body member 11 is formed with a central cylindrical bore 14 extending through its anterior face 12 and its posterior face 13.

A converging lens 15 is fixed within bore 14 at the anterior side of body member 11, and a converging lens 16 is fixed within the bore at the posterior side of the body member. The diverging lens 16 is thus aligned with the converging lens 15 but is spaced rearwardly of the converging lens by the cavity defined by bore 14. The two lenses 15 and 16 thus define a Galilean telescopic system commonly used in opera glasses.

Such a telescopic system, when incorporated in an intraocular insert implanted into the human eye, in place of the natural crystalline lens, increases the visual field that the patient enjoys, thereby enabling the patient to read fine print without the use of an outside telescope. Thus, the normal eye movements in the reading process are preserved, and the patient does not need to move his or her head from one side of the line to the other in order to read, as generally required when using external telescopic spectacles.

The two lenses 15 and 16 may be made of the same material as presently used for making intraocular lenses, such as plastic (e.g., methyl methacrylate), glass, sapphire or the like. The body member 11 may be of the same material. The cavity 14 between the two lenses 15 and 16 may be filled with air, a gas, or a suitable liquid such as water.

Figure 2:
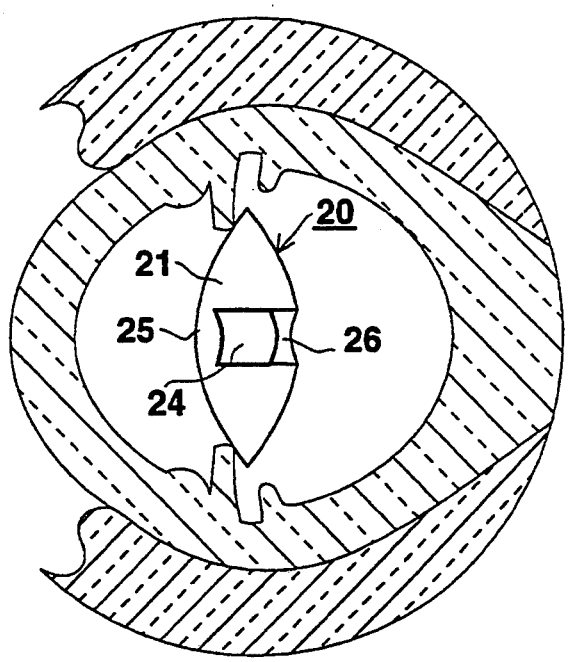
FIG. 2 is a horizontal section through the eye illustrating a second embodiment of intraocular insert constructed in accordance with the present invention.

FIG. 2 illustrates an intraocular insert, generally designated 20, similar to insert 10 of FIG. 1, and also including a body member 21 formed with a central cylindrical cavity 24 covered at its front side by a converging lens 25 facing the anterior side of the eye, and at its rear side by a diverging lens 26 facing the posterior side of the eye. In FIG. 2, however, the converging lens 25 is integrally formed with the body member 21, whereas the diverging lens 26 is formed as a separate element and is fixed, as by an adhesive or a weld, in the rear part of the cylindrical cavity 24 of the body member.

It will be seen that in the constructions of both FIGS. 1 and 2, the outer periphery of the anterior face of the converging lens (15, 25) is substantially flush with the anterior face of the body member 11; and similarly, the outer periphery of the posterior face of the diverging lens (16, 26) is substantially flush with the posterior face of the body member 11, 21.

Figure 3:
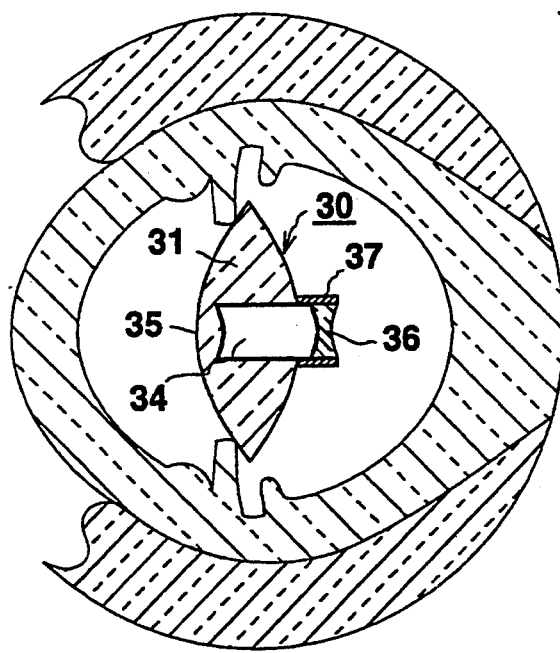
FIG. 3 is a horizontal section through the eye illustrating a third embodiment of intraocular insert constructed in accordance with the present invention.

FIG. 3 illustrates an intraocular insert, generally designated 30, also including a body member 31 formed with a central cylindrical bore 34 closed at the anterior end by a converging lens 35 and at the posterior end by a diverging lens 36. In this case, however, the converging lens 36 is mounted to a support 37 so that it extends rearwardly of the posterior face of the body member 30 and thereby produces a larger space between it and the converging lens 35. Such an arrangement increases the magnification of the intraocular insert.

In all other respects, the intraocular insert 30 illustrated in FIG. 3 is constructed and operates in the same manner as described above with respect to FIGS. 1 and 2.

While the invention has been described with respect to three preferred embodiments, it will be appreciated that these are set forth merely for purposes of example, and that many other variations may be made. For example the insert could include more than two lenses, combination lenses, holographic lenses, etc. In addition, the lenses could be mounted on a common holder (e.g., at the opposite ends of a cylindrical tube) fixed within a bore in the body member. Many other variations, modifications and applications of the invention will be apparent.

We claim:

1. An intraocular insert for implantation in the interior of a human eye having an anterior side and a posterior side, characterized in that said insert includes:
a converging lens carried by the insert to face the anterior side of the eye;
and a diverging lens carried by the insert in alignment with and spaced behind said converging lens to face the posterior side of the eye.

2. The intraocular insert according to claim 1, wherein said insert further includes a body member supporting said converging lens and diverging lens in spaced relation at the opposite ends of a cavity in the insert.

3. The intraocular insert according to claim 2, wherein said cavity is of cylindrical configuration.

4. The intraocular insert according to claim 2, wherein said converging lens and diverging lens are separate elements fixed to the body member at the opposite ends of said cavity.

5. The intraocular insert according to claim 2, wherein said converging lens is integrally formed with said body member at one end of said cavity, diverging lens is fixed to the body member at the opposite end of said cavity.

6. The intraocular insert according to claim 2, wherein the outer periphery of the anterior face of said converging lens is substantially flush with the anterior face of the body member.

7. The intraocular insert according to claim 2, wherein the outer periphery of the posterior face of the diverging lens is substantially flush with the posterior face of the body member.

8. The intraocular insert according to claim 2, wherein the posterior face of said diverging lens projects rearwardly of the posterior face of the body member.

9. An intraocular insert for implantation in the interior of a human eye having an anterior side and a posterior side, characterized in that said insert includes a combination of lenses constituting a Galilean telescope.

10. The intraocular insert according to claim 9, wherein said combination of lenses includes:
converging lens to face the anterior side of the eye;
and a diverging lens in alignment with and spaced behind said converging lens to face the posterior side of the eye.

11. The intraocular insert according to claim 10, wherein said insert further includes a body member supporting said converging lens and diverging lens in spaced relation at the opposite ends of a cavity which cavity is filled with a fluid.

12. The intraocular insert according to claim 11, wherein said cavity is of cylindrical configuration.

13. The intraocular insert according to claim 11, wherein said converging lens and diverging lens are separate elements fixed to the body member at the opposite ends of said cavity.

14. The intraocular insert according to claim 11, wherein said converging lens is integrally formed with said body member at one end of said cavity, and said diverging lens is fixed to the body member at the opposite end of said cavity.

15. The intraocular insert according to claim 11, wherein the outer periphery of the anterior face of said converging lens is substantially flush with the anterior face of the body member.

16. The intraocular insert according to claim 11, wherein the outer periphery of the posterior face of the diverging lens is substantially flush with the posterior face of the body member.

17. The intraocular insert according to claim 11, wherein the posterior face of said diverging lens projects rearwardly of the posterior face of the body member.

18. An intraocular insert for implantation in the interior of a human eye, comprising:
a body member having a convex front face facing the anterior side of the eye, and a convex rear face facing the posterior side of the eye, said body member being formed with a cylindrical cavity extending centrally therethrough and through its front and rear faces;
a converging lens located at the front part of the cylindrical cavity to face the anterior side of the eye;
diverging lens located in the rear part of the cavity to face the anterior side of the eye;
and a fluid filling said cavity between said converging and diverging lenses.

19. The intraocular insert according to claim 18, wherein the outer periphery of the anterior face of said converging lens is substantially flush with the anterior face of the body member, and the outer periphery of the posterior face of said diverging lens is substantially flush with the posterior face of the body member.

20. The intraocular insert according to claim 18, wherein the outer periphery of the anterior face of said converging lens is substantially flush with the anterior face of the body member, and the outer periphery of the posterior face of said diverging lens projects rearwardly of the posterior face of said body member.

* * * * *